United States Patent [19]

Vossen

[11] Patent Number: 4,906,565

[45] Date of Patent: Mar. 6, 1990

[54] METHOD FOR THE SELECTIVE DETECTION OF MICROBIAL NUCLEOTIDES

[75] Inventor: John G. H. M. Vossen, Nieuwstadt, Netherlands

[73] Assignee: Minnesota Mining and Manufacturing Company, St. Paul, Minn.

[21] Appl. No.: 842,628

[22] Filed: Mar. 21, 1986

[51] Int. Cl.⁴ .................. C12Q 1/48; C12Q 1/34; C12Q 1/02; C12Q 1/04

[52] U.S. Cl. ...................................... 435/15; 435/18; 435/29; 435/34

[58] Field of Search .............. 435/6, 18, 29, 34, 810, 435/259, 15

[56] References Cited

U.S. PATENT DOCUMENTS 3,745,090  7/1973  Chappelle et al. .
3,971,703  7/1976  Picciolo et al. .
4,014,745  3/1977  Fletcher et al. .
4,264,727  4/1981  Kolehmainen et al. .
4,303,752  12/1981 Kolehmainen et al. .
4,501,813  2/1985  Lovgren et al. .

FOREIGN PATENT DOCUMENTS 0123094  9/1979  Japan ...................................... 435/34

OTHER PUBLICATIONS

Chem. Abst. 96(7) issued Feb. 15, 1982, p. 492, 50798u, Vossen, J. G. H. M., "New Method for Rapid Detection . . . ATP Bioluminescence".
F. R. Leach, J. Appl. Biochem. 3:473–517 (1981).
CRC Handbook of Biochemistry, 2d ed., pp. C-139 to 140, H. A. Sober ed., The Chemical Rubber Co., Cleveland, Ohio (1970).
Riordan, J. F. and B. L. Vallee, Methods in Enzymol., vol. XXV, pp. 449–456 (1972).
Kenyon, G. L. and T. W. Bruice, Methods in Enzymol., vol. XLVII, pp. 407–430 (1977).
M. A. Valenzuela et al., Biochem. J. 133:755–763 (1973).
M. DeLuca et al., "Role of Sulfhydryl Groups in Firefly Luciferase", Biochem. 3:935–939 (1964).
M. Bárány et al., "Giftwirkungen auf die Kartoffel-Apyrase", Biochim. Biophys. Acta, 35:544–545 (1959) incl. translation.
J. W. Thorner and H. Paulus, "Glycerol and Glycerate Kinases", Chapter 14, pp. 487–508, *The Enzymes*, 3d ed., vol. XIII (1973).
"Lumac TM /Bacteriuria Screening Kit No. 4631", 1982.

Primary Examiner—Amelia Burgess Yarbrough
Assistant Examiner—Jeremy M. Jay
Attorney, Agent, or Firm—Donald M. Sell; Walter N. Kirn; Philip M. Goldman

[57] ABSTRACT

A method for the selective determination of microbial cells, in a sample suspected of containing both microbial and non-microbial cells, is described which involves the selective release and enzymatic inactivation of non-microbial nucleotides, followed by the rapid and specific inhibition of the inactivating enzyme and the release and detection of microbial nucleotides in an appropriate assay, such as a bioluminescent assay.

9 Claims, No Drawings

METHOD FOR THE SELECTIVE DETECTION OF MICROBIAL NUCLEOTIDES

TECHNICAL FIELD

This invention relates to the selective determination of microbial cells in a sample suspected of containing both microbial and non-microbial cells. In another aspect it relates to the use of an assay, such as a bioluminescent assay, for the detection of microbial nucleotides as a method of determining the presence, number or biomass of microbial cells in a sample, and to the inactivation or removal of non-microbial nucleotides prior to the detection of microbial nucleotides.

BACKGROUND OF THE INVENTION

Present bioluminescent assay methods for determining the presence, number or biomass of microbial cells in a sample which may also contain non-microbial cells require longer processing times than desired. These methods are generally based on the detection of microbial nucleotides, such as adenosine triphosphate (ATP). In a typical assay, microbial cells can be treated so as to release their ATP into solution where it can react with bioluminescent assay reagents, such as firefly luciferase enzyme and luciferin substrate, in the presence of magnesium and oxygen, to produce photons. These photons are detectable and their numbers can be correlated with the amount of ATP, and in turn, with the number or mass of cells originally present. See generally, U.S. Pat. Nos. 3,745,090, 3,971,703, 4,014,745, 4,264,727, 4,303,752 and 4,501,813, and Leach, J. Appl. Biochem. 3, 473–517 (1981).

The longer-than-desired processing times occur because of measures that must first be taken to "remove" from the assay nucleotides of an non-microbial cells which are present in the sample. U.S. Pat. No. 3,745,090 suggests removal of non-microbial ATP by: treating the sample to release ATP specifically from non-microbial cells; hydrolyzing or "inactivating" the released ATP by addition of an "ATP-hydrolyzing enzyme" such as an ATPase or, more commonly, an apyrase, both of which are hydrolase enzymes; and then inactivating or destroying the enzyme so that it does not affect the ATP later released from the microbial cells. The microbial ATP would then be released and detected by means of a bioluminescent assay.

U.S. Pat. No. 3,745,090 suggests certain approaches for inactivating or destroying apyrase activity. Some of these suggested approaches would act by nonspecifically and irreversibly destroying all proteins in the sample (including the enzymes), such as by heat or acid treatment. Such approaches are inconvenient, often hazardous, and radical in that they would very likely destroy microbial cells as well, thereby affecting the sensitivity and accuracy of the assay.

While this patent also suggests the use of "enzyme inhibitors", apparently none have yet been shown to be inhibitory to an ATP-hydrolyzing enzyme, e.g., apyrase, yet suitable for use in such methods, e.g., in terms of being compatible with the reactants, reactions and/or readings of a subsequent bioluminescent assay.

As a result, in spite of the approaches suggested in U.S. Pat. No. 3,745,090, the typical approach in commercial applications to negate the potential effect of the commonly used hydrolase enzyme apyrase on microbial ATP has been to simply employ low concentrations of apyrase, as set forth in U.S. Pat. No. 4,303,752. At these low concentrations the time needed for apyrase to inactivate the non-microbial ATP becomes correspondingly longer. When the inactivation of non-microbial ATP is complete however, microbial ATP can then be released and quickly assayed in spite of the fact that a portion of it will be inactivated in the process by the still-present, still-active apyrase.

The optimal amount of apyrase that is used in a particular application is therefore generally the amount that allows the shortest possible "inactivation time" for non-microbial nucleotides, while still allowing microbial ATP to be detected. As a result, apyrase concentrations are generally quite low, and the inactivation of non-microbial ATP in turn becomes the major time-consuming step in the overall procedure Indeed, many of the commercially available bioluminescent assays for the detection of microbes, e.g., in body fluids and food samples, employ time periods on the order of 10–60 minutes for the complete inactivation of non-microbial ATP by apyrase. This can be compared to the other steps of a typical assay, such as the adding and mixing of reagents, the release of microbial ATP and the production and counting of photons, which are generally accomplished in a matter of minutes, if not seconds, using automated procedures specifically adapted to these assays. In many applications, e.g., where large numbers of samples have to be routinely processed, it would be greatly beneficial to be able to achieve shorter "inactivation times" for non-microbial nucleotides, preferably in a manner compatible with automated assay procedures.

Clearly a method is desirable for the rapid inactivation of non-microbial nucleotides, where the method used for the inactivation can itself be specifically, quickly and effectively negated in a manner that does not interfere with a subsequent assay for microbial nucleotides.

SUMMARY OF THE INVENTION

The present invention provides a method for the selective determination of microbial nucleotides that is useful for a sample suspected of containing both non-microbial and microbial cells, comprising the steps of:

(1) selectively releasing non-microbial nucleotides, (2) inactivating substantially all of the released non-microbial nucleotides by use of an effective amount of an inactivating enzyme, other than a hydrolase, which can be inhibited by a specific inhibitor, (3) inhibiting substantially all of the inactivating enzyme by use of an effective amount of a specific inhibitor, (4) selectively releasing microbial nucleotides, and (5) detecting a statistically significant amount of released microbial nucleotides by means of an appropriate assay.

The method can be used for the mere detection of microbial cells or for the determination of the number or biomass of microbial cells, e.g., by correlating the amount of microbial nucleotides detected in a bioluminescent assay with the concentration of nucleotides per cell. As a result of the method of the invention, inactivating enzymes can be used in high enough concentrations to enable very short "inactivation times" and thus shorten appreciably the overall time required per determination. The method is readily adaptable and compatible with the automated assay procedures currently employed to perform bioluminescent assays.

The method can generally even be used in spite of the possibility that an inhibitor is active against a reagent of the bioluminescent assay itself, since the concentration of effective inhibitor relative to the bioluminescent assay reagent can be kept low enough to allow an activity of the bioluminescent assay reagent sufficient to ensure adequate sensitivity of the assay.

DETAILED DESCRIPTION OF THE INVENTION

As used herein the term "assay" refers to any assay which detects a nucleotide contained in or produced by a living cell.

The term "nucleotide" refers to any purine, pyrimidine, or pyridine nucleotide which is detectable, directly or indirectly, by an assay.

The term "inactivating enzyme", as used herein, refers to an enzyme which acts in such a way as to render a nucleotide undetectable in an assay in which the nucleotide would otherwise be detectable, i.e., "inactivate" a nucleotide.

Unless otherwise apparent, the term "inhibit" and variations thereof, including "specific inhibitor", refer to any direct or indirect interaction of a molecule, compound, reagent and/or condition with an inactivating enzyme, which is specific in that all or most other proteins in the sample containing the enzyme are not irreversibly destroyed thereby, as for instance by heat or acid, and where the interaction is at least partly responsible for diminishing the activity of the enzyme in such a way and to such a degree that will allow a statistically significant amount of microbial nucleotides, if present, to be detected by an assay.

"Non-microbial" and "microbial" as used herein are mutually exclusive and refer to cells which are susceptible to the selective release of nucleotides, such as by non-ionic and ionic surface active agents, respectively, as disclosed in U.S. Pat. No. 4,303,752, the disclosure of which is hereby incorporated by reference. "Non-microbial" shall also include any free or other nucleotides present in a sample, from whatever source, which are to be inactivated prior to the release of microbial nucleotides present in that sample. The terms "first releasing agent" and "second releasing agent" as used herein will refer to the agents and/or conditions used for the release of non-microbial and microbial nucleotides, respectively, such as non-ionic and ionic surface active agents as described in U.S. Pat. No. 4,303,752 and the agents and conditions disclosed in U.S. Pat. No. 3,745,090, the disclosure of which is hereby incorporated by reference.

"Statistically significant" as used herein refers to a level of detection of microbial nucleotides which is suitable for the purpose of an assay. For instance, mere detection of microbial ATP, as in sterility testing will require a less strict or exacting combination of assay conditions for statistical significance (i.e., less than maximum sensitivity or accuracy) than will an assay meant to accurately enumerate microbes. In the former situation for instance, it may be sufficient to determine if the detectable nucleotide level is greater or lesser than a pre-determined value. That pre-determined value can be calculated on a case by case basis by taking into account the relative activities and concentrations of reactants and any other relevant factors which impact on the sensitivity or accuracy of the assay. The word "substantially" as used herein refers to an amount or degree that will enable a statistically significant assay to be performed.

Inhibitors suitable for use in the present invention must meet two basic criteria: (1) they must be able to directly or indirectly interact with an inactivating enzyme in a specific manner, whereby the interaction is at least partly responsible for diminishing the activity of the enzyme, and (2) they must act in such a way and to such a degree that will allow a statistically significant amount of microbial nucleotides, if present, to be detected by an assay.

As for the first criterion, the inhibitor is preferably a molecule, compound, reagent and/or condition that is reactive, directly or indirectly, with the enzyme.

Some enzymes can be specifically inhibited, for instance, by "feedback inhibition" by the very products of the enzyme-catalyzed reaction. With such an enzyme the addition of the relevant product would inhibit continued enzyme activity, generally by binding of the product at an essential (e.g., active or allosteric) site on the enzyme. Similarly, many enzymes are specifically inhibitable through interactions of a molecule, compound, reagent and/or condition with a particular group or groups that are contained in the enzyme and are in some way essential to the inactivating (i.e. catalytic) activity of the enzyme. Groups which can be interacted with in this manner include but are not limited to amino, imidazole, quanidinyl, indole, thio ether, disulfide, hydroxyl, phenol, and carboxyl groups.

The site or specific group or groups that are interacted with need not be at the enzyme's active site and the inhibition of the inactivating enzyme can be reversible or irreversible. Similarly the inhibitor may act by removing, from solution or from the enzyme, another molecule or compound that is essential to the enzyme's activity. For instance if a particular enzyme requires the presence of a divalent cation for its activity, the addition of a proper chelator could inactivate the enzyme by effectively removing the cation In this and similar ways the inhibitor, here the chelator, would be considered an indirect inhibitor of the enzyme.

Preferred inhibitors will show an optimal combination of such factors as specificity and speed in their inhibition of the inactivating enzyme, minimal interference (e.g., by quenching) with the subsequent assay, and solubility, cost, availability, safety, stability and purity.

Preferred inhibitors are available commercially, and can be used under conditions that are well described in the art. Generally the inhibitor should function under the conditions of temperature, pH and so on, chosen for the overall assay.

A preferred group of inhibitors are reagents, particularly those that are specific for the sulfhydryl groups of enzymes. Some of these are set forth, for example, in CRC Handbook of Biochemistry, 2d, Sober ed., 1970, Table C-139. The specificity of a particular inhibitor for sulfhydryl groups can also be assayed by methods such as those disclosed in Riordan, et al., Methods Enzm. Vol. XXV, pp. 449-464, the disclosure of which is hereby incorporated by reference.

Particularly preferred inhibitors are those classified as "Blocking and Labeling Group" inhibitors as described in Kenyon, G. L. And T. W. Bruice, Methods in Enzymol. Vol XLVII, pp. 407-430. Preferred irreversible inhibitors among this group include but are not limited to N-ethylmaleimide, organomercurials, iodoacetate, and iodoacetamide and preferred reversible inhibitors include but are not limited to aryl halides such as dinitrofluorobenzene.

As for the second criterion of an inhibitor, i.e., allowing a statistically significant assay to be performed, it is important to note that the inhibitor need not be totally without effect on the assay. Rather, it is merely required that given a judicious combination of such factors as the relative times, activities and concentrations of the reagents involved, that interference with the detection of microbial nucleotides is minimized, at least to a degree where a statistically significant amount of microbial nucleotides can be detected in spite of the presence of the inhibitor. In fact, preferred inhibitors of the invention such as those specific for sulfhydryl groups, are very likely inhibitory to sulfhydryl-sensitive bioluminescent assay enzymes, such as firefly luciferase. Given the method of the invention however, the amount of luciferase that is inhibited is tolerable.

The effect of a particular inhibitor on a bioluminescent assay can be experimentally determined in a variety of ways, such as by preparing and comparing assay samples containing varying concentrations of that inhibitor with samples serving as controls. If the level of sensitivity of the assay that is desired for a particular application can be achieved at an inhibitor concentration that is sufficient to inhibit the inactivating enzyme, that inhibitor is suitable for consideration for use in the method of the invention.

The commonly used hydrolase enzyme apyrase therefore is not suitable for use in the method of the present invention in view of the apparent inability to identify an inhibitor that meets this second criterion. Apyrase has been shown to be not susceptible to inhibition, for instance, by sulfhydryl group reagents. See, e.g., Valenzuela et al., Biochem. J. 133:755–763 (1973).

Enzymes that are suitable for use in the present invention as inactivating enzymes are therefore the non-hydrolase enzymes; and these must also meet two basic criteria: (1) they must act in such a way as to render the pertinent non-microbial nucleotide undetectable in an assay in which the nucleotide would othewise be detectable, and (2) they must be capable of being interacted with in a specific manner so as to substantially prevent or inhibit that ability.

Enzymes that meet the first requirement are known, and include enzymes that act directly on nucleotides as substrates, e.g., to phosphorylate another molecule, as well as enzymes that act on other substrates in coupled endothermic reactions but which require a nucleotide, e.g., as a source of energy or reducing equivalents, to drive those reactions.

Enzymes are best classified by reference to the classification recommended by the Nomenclature Committee of the International Union of Biochemistry, Enzyme Nomenclature (1978). Under this enzyme classification ("EC"), nucleotide-inactivating enzymes suitable for purposes of the method of the invention include certain enzymes in the oxidoreductase, transferase, lyase, isomerase and ligase classes.

Preferred inactivating enzymes are those that show a high level of nucleotide inactivating activity, as well as a high sensitivity to specific inhibition. Also preferred are enzymes which catalyze exothermic reactions, e.g., those which result in the complete conversion of the nucleotide rather than establishing an equilibrium state between the nucleotide and its product. Further preferred enzymes are those which, because of their cost, availability, safety, solubility, stability and purity are amenable to widespread, reproducible, sensitive and inexpensive use in routine analyses.

Examples of preferred inactivating enzymes are those categorized as transferases in EC group 2, and particularly preferred are phosphotransferases (commonly known as kinases) in EC group 2.7. In terms of activity, enzymes in group 2.7 are distinguished primarily according to the acceptor group involved. Phosphotransferases in group 2.7.1 transfer a phosphate group to an alcohol group of an acceptor molecule; in group 2.7.2 to a carboxyl group, in group 2.7.3 to a nitrogenous group; and in group 2.7.4 they transfer the phosphate group to another phosphate group, as in the case of an adenylate kinase. Reactions catalyzed by enzymes in the first group (2.7.1) are generally irreversible, whereas those of the other three groups are generally reversible. Reversibility of the reaction is not generally a critical factor in the method of the invention.

Preferred phosphotransferases are hexokinase, and acetate kinase and chemical modifications thereof as well as those classified as EC 2.7.1.30, commonly called glycerokinases (also known as glycerol kinases and ATP: glycerol 3-phosphotransferases). Glycerokinases catalyze the transfer of a phosphate group from an ATP donor molecule to a glycerol acceptor molecule according to the equation

$$\text{ATP} + \text{glycerol} \xrightarrow{\text{Mg}^{+2}} \text{ADP} + \text{glycerol 3-phosphate.}$$

A variety of glycerokinases exist in nature. Each functions by converting glycerol to glycerol 3-phosphate, a form which can enter various synthetic pathways such as those leading to glycogen, triacylglycerols and so on.

Suitable glycerokinases can be obtained commercially, for example from Sigma Chemical Company, St. Louis, Missouri, which has available the microbial enzymes derived from *Candida mycoderma, Candida utilis* and *Escherichia coli*. Glycerokinase can also be obtained from non-microbial (e.g., mammalian) sources. Glycerokinases from different sources can not only differ in terms of their level of inactivitating activity, but also, e.g., in terms of their susceptibility to inhibition by various inhibitors. For instance, glycerokinases from mammalian sources are generally more susceptible to inhibition by iodoacetamide, whereas those from bacterial sources are more susceptible to inhibition by organomercurials.

The physical form or activity of the inactivating enzyme is not critical (e.g., crystalline suspensions, lyophilized powders, or solutions), if the form and activity is suitable for use in the method of the invention.

If necessary, each inactivating enzyme is generally used in the method of the invention with an added, i.e., exogenous, amount of its respective acceptor molecule. Reliance upon a suitable endogenous supply of acceptor molecules is possible when the acceptor molecule is expected to be naturally present in sufficient quantities in the sample, but to ensure an adequate level of activity of the inactivating enzyme, the addition of acceptor molecule at a concentration effective to provide such activity is preferred.

The preferred acceptor molecule for glycerokinase, for example, is glycerol which is widely and inexpensively available. The preferred concentration of glycerol will generally be between about 1 mM to about 30 mM and most preferably about 1 mM to about 10 mM. Glycerokinase will, however, phosphorylate other acceptor molecules as well, such as dihydroxyacetone, 1-glyceraldehyde, 1-glyceraldehyde acetate and so on.

Each inactivating enzyme will also preferably be used under such other conditions and with such cofactors as are necessary to its activity, so long as those conditions and/or cofactors do not significantly detrimentally affect the subsequent assay. The preferred glycerokinase enzyme, for instance will generally be used in the presence of suitable divalent metal cations such as $Mg^{+2}$. Some glycerokinases are stimulated by $Mg^{+2}$, or other similar cations, whereas others have an absolute requirement for such cations. The optimal $Mg^{+2}$ concentration for the use of glycerokinase will depend in part on other factors, such as the ATP concentration, but will generally be between about 1 mM and about 10 mM, most preferably about 3 mM to about 7 mM.

Similarly, the inactivating enzyme will be used at a pH range that is suitable for enzyme activity. For glycerokinase, for instance, this will be preferably between about pH 6 and about pH 10 and most preferably between about pH 7 and about pH 8. Other adjuvants and conditions are well described in the literature and generally commercially available for each inactivating enzyme.

The method of the present invention begins with a sample suspected of containing both non-microbial and microbial cells. Since non-microbial cells generally contain more nucleotides eer cell than microbial cells contain, the sample need not contain numerically more non-microbial cells than microbial cells. It is sufficient reason to employ the method of the invention if there is reason to suspect that there are, or could be, enough nucleotides, e.g., naturally occurring or contaminating the sample, and either in solution or present in non-microbial cells, to distort or cast doubt on the ability to determine microbial cells.

Typical samples to which the method of the invention can be applied include body fluids such as urine and blood, dairy products, prepared foods, drinks and juice, cosmetics and pharmaceuticals, environmental samples and research applications (e.g., antibiotic testing). The sample is obtained, handled, and prepared according to known techniques, e.g., to enrich a sample, as by preincubation or filtration, or to solubilize a sample, remove turbidity, or avoid undue color or viscosity. Preferably the samples will be prepared as single cells in suspension or as mono- or bi-layers of cells according to methods known in the art.

As an initial step of the method of the invention nucleotides are selectively released from non-microbial cells. This is preferably accomplished by the use of a first releasing agent, e.g., to lyse or permeabilize the non-microbial cells. The first releasing agent can be any of a variety of compounds or conditions which selectively release non-microbial nucleotides.

Preferably, the first releasing agent will be a nonionic surface active agent, such as ethoxylated alkyl phenols or fatty acid poly glycol ethers as described in U.S. Pat. No. 4,303,752.

The first releasing agent is added to the sample solution at an effective concentration, i.e., one sufficient to release substantially all non-microbial nucleotides within a desired period of time. Using a preferred first releasing agent, the membrane of non-microbial cells becomes permeable, allowing nucleotides to rapidly and freely diffuse out of the cells and into the extracellular environment. Using a preferred first releasing agent, most nucleotides will be released from non-microbial cells within about 15 to 60 seconds when the non-microbial cell number does not exceed approximately 10 million per milliliter. Since the non-microbial cells will generally occupy only a small percentage of the volume of the sample, after the cells become permeable the majority of nucleotides will exist outside the cells. The sample can, optionally, be incubated, e.g., for up to about 60 minutes at room temperature or at any other suitable temperature, but preferably between $+2°$ C. and $+40°$ C. to ensure the maximum release of the non-microbial nucleotides.

As a further step, substantially all of the released non-microbial nucleotides are inactivated by use of an inactivating enzyme which can be inhibited by a specific inhibitor. The inactivating enzyme can be added to the sample before, with and/or after the addition of the first releasing agent. The timing of the addition of inactivating enzyme is generally not critical since its actual inactivating activity will not occur until after nucleotides are released, regardless of when the enzyme is added. For convenience and speed, it is preferable to add the enzyme simultaneously with the addition of the first releasing agent.

The enzyme concentration is not as critical as it is in many current assay methods which incorporate apyrase, precisely because the enzymes of the present invention can be inhibited, essentially at will, and at whatever concentration happens to be added. Similarly the actual concentration of enzyme will vary according to the type and source of enzyme, the enzyme's activity, the level of non-microbial nucleotides anticipated and so on, as will be readily apparent to one skilled in the art.

Generally, the preferred inactivating enzymes of the present invention will be present in an effective concentration, i.e., a concentration that is able to inactivate the anticipated nucleotide concentration in the desired period of time, as determined by calculation or preferably by simple experimentation. Preferably along with the inactivating enzyme, any respective acceptor molecule and other compounds, cofactors or molecules required for enzymatic activity will also be added.

The sample is incubated, preferably with agitation, for a time sufficient to allow the inactivating enzyme to inactivate substantially all of the nucleotides released from the non-microbial cells.

By virtue of its necessarily low concentration, the enzyme commonly in use to inactivate non-microbial nucleotides, i.e., apyrase, requires incubation times on the order of 10–60 minutes, depending in large part on the type of sample. According to the method of the present invention, inactivating enzyme can be added in concentrations sufficient to reduce these incubation times correspondingly, generally to at least one-half and preferably to one-fourth or less of the time required in a comparable conventional method using low concentrations of apyrase. The incubation time according to the method of the invention will therefore be preferably about 10 minutes or less and most preferably about 5 minutes or less. The proper incubation time can be determined largely by consideration of the anticipated concentration of non-microbial nucleotides, and the relative concentrations and activities of the inactivating enzyme and inhibitor. A proper balance of these factors, as will be readily apparent to one skilled in the art, can achieve a sufficient degree of inactivation in a short period of time so as to allow the subsequent release and determination of microbial nucleotides.

As a further step, substantially all of the inactivating enzyme is inhibited by use of a specific inhibitor. The inhibitor is preferably added directly to the solution containing inactivating enzyme and non-microbial nucleotides in such amounts, at such times and under such conditions that will enable the inhibition to be accomplished in a short period of time, e.g., on the order of 60 seconds or less with agitation.

The amount of inhibitor that is added will be dependent on such factors as the type, source concentration, and sensitivity of the inactivating enzyme and the concentration and sensitivity of any reagents in the subsequent assay. While the actual inhibitor concentration is not critical, it will preferably be an effective concentration, i.e., it will be sufficient to inhibit substantially all of the inactivating enzyme, yet allow a statistically significant detection of microbial nucleotides to be made. Preferably the inhibitor will not be present in large excess over the effective concentration, and will be able to inhibit the inactivating enzyme within a period of time that allows a statistically significant assay of microbial nucleotides to be made. The actual concentration of inhibitor will vary significantly depending in part on the inhibitor chosen and the inactivating enzyme used, but can be determined by simple experimentation by one skilled in the art.

Optionally, additional measures may be taken after the inhibition of inactivating enzyme, particularly if the specific inhibitor happens to be present at a concentration in excess of the enzyme and is itself inhibitory towards any of the assay reagents to be added. Since these assay reagents will typically be among the more expensive components of the method of the invention, and will typically be commercially available for these uses in kits containing predetermined amounts, it may be advisable under some circumstances to first negate some or all of the effects of any excess inhibitor on the reagents before the reagents are themselves inhibited. In this way it can be assured that an effective and preferably known amount of assay reagents will remain active.

One such measure which might be taken is to add a compound to the solution which is itself capable of reacting with and therefore "tying up" excess inhibitor. For example when the inhibitor is a sulfhydryl group reagent, addition of the amino acid cysteine, which contains a sulfhydryl group, would compete for the inhibitor with a sulfhydryl-sensitive assay reagent. If the binding kinetics of cysteine with the inhibitor were compared to those of the assay reagent, one skilled in the art could readily determine the concentration of cysteine necessary to yield the desired level of uninhibited assay reagent.

Inhibitor is preferably added before the release of microbial nucleotides, or at least before the inactivating enzyme has the opportunity to inactivate so many microbial nucleotides that their detection is no longer statistically significant. Inhibitor is preferably added simultaneously with the second releasing agent in the method of the invention, i.e., at the same time nucleotides are beginning to be released from microbial cells. If various factors are controlled with respect to each other, such as the concentration and type of inactivating enzyme, inhibitor and releasing agent, the inhibitor can effectively inhibit the inactivating enzyme within a matter of seconds. Since the release of microbial nucleotides is also frequently on the order of seconds, the judicious use of both inhibitor and releasing agent, as will be readily achieved by persons skilled in the art, will allow substantially all of the non-microbial nucleotides, and perhaps even some of the microbial nucleotides to be inactivated by enzymatic activity, yet will allow a statistically significant amount of microbial nucleotides to remain.

As a further step, the microbial nucleotides are selectively released. This can be accomplished simultaneously with, or after the addition of inhibitor, by the addition of an effective amount of a second releasing agent.

Preferred second releasing agents are ionic surface active agents as disclosed in U.S. Pat. No. 4,303,752. A particularly preferred second releasing agent is a mixture of a quaternary ammonium salt and an ethoxylated amine, ethoxylated diamine, polyethylene glycol ester of fatty acids, or ethoxylated amide. Using preferred second releasing agents, at suitable concentrations, such as on the order of 0.05–0.5% by volume, the cell membrane and cell wall of microbes will generally be sufficiently permeabilized to allow the rapid release of nucleotides within about a 15–60 second mixing time.

As a further step, a statistically significant amount of the released microbial nucleotides is detected by means of an appropriate assay, such as a bioluminescent or chemiluminescent assay. Other suitable assays which can be used according to the method of the invention include photometric, spectrophotometric, fluorescent and other assays known in the art which can be used to detect, directly or indirectly, the microbial nucleotides present.

Preferably, the assay will be a bioluminescent assay. In a typical assay, an aliquot, e.g., 50 $\mu$l–1.0 ml, of the sample solution is mixed with the appropriate bioluminescent reagent(s), e.g., the firefly luciferase-luciferin reagent for ATP, and the resultant light emission is measured by photometric means according to methods known in the art.

The preferred reagents for the bioluminescent detection of ATP are the luciferase-luciferin reagents. A typical commercial reagent ("Lumit PM", Lumac/3M, The Netherlands) includes luciferase enzyme, purified from fireflies; synthetic D-luciferin, a cofactor for the enzyme; a stabilizer such as bovine serum albumin; and a compound to protect the luciferase sulfhydryl groups during storage, such as dithiothreitol. This reagent is typically freeze dried and supplied under vacuum in an opaque vial. The reagent can be resuspended in buffer and used according to the manufacturer's instructions.

The method of the invention will typically be carried out in a buffered solution, and each ingredient will be either prepared in the same buffer or in another solution which does not detrimentally impact on the efficacy of the buffered solution. For instance a commercially available buffer solution containing 25 mM Hepes and 7.5 mM $MgSO_4$ at pH 7.75 ("Lumit Buffer", Lumac/3M) is particularly well suited for such purposes.

The inactivating enzyme, and its corresponding specific inhibitor, used in the method of the invention can be prepared and packaged in a manner that facilitates their incorporation into a rapid and automated application of the method to a large number of samples. For example, the enzyme and inhibitor can be individually packaged (e.g., in vials) in predetermined amounts, optionally with other components of an assay and/or with adjuvants such as preservatives. Instructions for their dilution and use can then accompany these predetermined amounts in order to form or augment kits useful for the selective determination of microbial nucleotides.

Other reagents suitable for the method of the present invention are available commercially and can be prepared and used in ways known to those skilled in the art.

Suitable means for the detection of photons produced in a bioluminescent or chemiluminescent reaction include a variety of commercially available photometric instruments, including photodiode instruments and photon counting instruments. In a photon counting instrument, e.g., a "Biocounter" available commercially from Lumac/3M, the light produced in a bioluminescent reaction is integrated over a fixed time interval (e.g., 10, 30 or 60 seconds).

Ideally the photometric instrument will incorporate an automatic and rapid pipetting apparatus, thereby allowing closer control over the time, accuracy and conditions of the steps involved in performing the assay.

The measurement derived from the preferred photometric detection of photons, (such as Relative Light Units (RLU's) derived from a photon counting instrument) can be correlated with the amount of microbial nucleotides. This determination, in turn, can be used in a variety of ways known in the art, e.g., it can be compared to a predetermined threshold level in a screening assay for contamination or sterility, or it can be correlated with the numbers or mass of cells present. For instance a standard curve can be derived using a conventional plate count method and used to correlate colony forming units (CFU)/ml with RLU's.

The following examples are given to illustrate, but not limit the scope of this invention. Throughout the examples, a "+" indicates that a particular ingredient was present at the concentration indicated, and a "—" indicates that it was absent. All concentrations listed in tables are final concentrations in the sample before addition of the bioluminescent reagents, unless otherwise indicated.

The samples were each assayed according to standard bioluminescent techniques in a photon counting instrument (Biocounter M2010, Lumac/3M). According to these techniques, a 50 μl or 100 μl aliquot of the sample to be assayed is transferred to a cuvette. The cuvette is placed in the counter, and there 100 μl of the bioluminescent reagents (Lumit PM) is added. Simultaneously, the counter measures emitted light using a 10 second integration period, and yields the result in terms of Relative Light Units ("RLU").

EXAMPLE 1

The ATP-inactivating ability of the enzyme glycerokinase, and the effectiveness of p-chloromercuribenzoic acid ("PCMB"), an organomercurial, as an inhibitor of that enzyme were determined to assess their usefulness in a method of the invention.

Materials:

Buffer: Lumit Buffer, Lumac/3M, The Netherlands, 25 mM Hepes, 7.5mM MgSO4 (pH 7.75).
ATP: Lumac/3M, contents of one vial (10 μg) reconstituted to 10 ml with buffer. This solution was further diluted 1:10 with buffer.
Magnesium sulfate: Merck GmbH, Darmstadt, German Fed. Rep., 500 mM in bidistilled water.
Glycerol acceptor molecule: Merck, 300 mM in bidistilled water.
Glycerokinase enzyme: Sigma Chemical Co., St. Louis, MO, 80 U/mg, 2 mg/ml in 3.2 M ammonium sulfate. Final concentration, 1.6 U/ml.
Inhibitor: p-Chloromercuribenzoic acid (PCMB), Sigma, 0 mM in 25 mM Hepes, 0.2 N NaOH (solution A). This solution was further diluted with buffer to give PCMB concentrations of 10 mM (solution B) or 1.0 mM (solution C).
Luciferase-luciferin: Lumit PM, Lumac/3M, contents of a vial reconstituted to 7.0 ml with buffer.

Protocol: the following samples were prepared:

| Sample | Buffer (μl) | ATP (μl) | MgSO4 (μl) | Glycerol (μl) | Glycerokinase (μl) | PCMB (μl, solution) | |
|---|---|---|---|---|---|---|---|
| 1 | 900 | 50 | 10 | 10 | 10 | 20 | A |
| 2 | 910 | 50 | 10 | 10 | 10 | 10 | A |
| 3 | 870 | 50 | 10 | 10 | 10 | 50 | B |
| 4 | 910 | 50 | 10 | 10 | 10 | 10 | B |
| 5 | 870 | 50 | 10 | 10 | 10 | 50 | C |
| 6 | 910 | 50 | 10 | 10 | 10 | 10 | C |
| 7 | 920 | 50 | 10 | 10 | 10 | 0 | — |

Assay: Glycerol was added last to the samples to initiate the enzyme's activity. Before glycerol was added a 50 μl aliquot was taken from all samples. ATP levels in those aliquots (expressed in RLU) were determined as time zero values. Next glycerol was added to the mixtures and further 50 μl aliquots were taken at 5, 10, and 15 minutes. ATP in all aliquots was measured by bioluminescent means as described. Results:

TABLE 1

| | Relative Light Units (RLU) | | | | |
|---|---|---|---|---|---|
| Sample | 0 min. | 5 min. | 10 min. | 15 min. | PCMB (mM) |
| 1 | 7987 | 7245 | 7905 | 7568 | 2 |
| 2 | 8802 | 9437 | 9329 | 9591 | 1 |
| 3 | 9041 | 8800 | 8617 | 9028 | 0.5 |
| 4 | 9499 | 9560 | 9253 | 9421 | 0.1 |
| 5 | 9003 | 9048 | 8727 | 9049 | 0.05 |
| 6 | 9065 | 9121 | 8982 | 3913 | 0.01 |
| 7 | 6572 | 8 | 13 | 9 | 0 |

Conclusions: As can be seen from TABLE 1, glycerokinase is an effective inactivating enzyme for ATP (see Sample 7), and PCMB is a very effective inhibitor of glycerokinase (since much of ATP was protected from inactivation in Samples 1-6). Even at a final concentration of 0.01 mM PCMB, glycerokinase seems to be sufficiently inhibited at the concentrations and within the times chosen.

EXAMPLE 2

The effect of p-Chloromercuribenzoic acid inhibitor on the bioluminescent assay of ATP was evaluated for use in a method of the invention.

Protocol: Using PCMB and other materials as prepared in EXAMPLE 1, the following samples were prepared.

| Sample | Buffer (μl) | ATP (μl) | PCMB (μl, solution) | |
|---|---|---|---|---|
| 1 | 850 | 50 | 100 | A |
| 2 | 900 | 50 | 50 | A |
| 3 | 940 | 50 | 10 | A |
| 4 | 900 | 50 | 50 | B |
| 5 | 940 | 50 | 10 | B |
| 6 | 900 | 50 | 50 | C |

-continued

| Sample | Buffer (μl) | ATP (μl) | PCMB (μl, solution) | |
|---|---|---|---|---|
| 7 | 940 | 50 | 10 | C |
| 8 | 950 | 50 | 0 | — |

Assay: from each sample triplicate 100 μl aliquots were taken. In those aliquots ATP was measured as described.
Results:

TABLE 2

| Sample | RLU 1 | 2 | 3 | mean | % of control | PCMB (mM) |
|---|---|---|---|---|---|---|
| 1 | 11 | 10 | 10 | 10 | <1% | 10 |
| 2 | 11 | 10 | 9 | 10 | <1% | 5 |
| 3 | 14576 | 13556 | 12956 | 13696 | 75 | 1 |
| 4 | 18190 | 18413 | 17824 | 18142 | 99 | 0.5 |
| 5 | 17914 | 18720 | 18505 | 18246 | 99 | 0.1 |
| 6 | 17984 | 17423 | 17118 | 17508 | 95 | 0.05 |
| 7 | 17959 | 18219 | 17484 | 17887 | 97 | 0.01 |
| 8 | 18578 | 18136 | 18060 | 18358 | 100 | 0 |

Conclusions: There are concentrations of PCMB shown in EXAMPLE 1 to be effective in inhibiting glycerokinase which do not significantly interfere with a bioluminescent assay (e.g., 0.01–1mM). Therefore glycerokinase enzyme/PCMB inhibitor combination is a useful one ofr practise of the present invention.

EXAMPLE 3

The effectiveness of dinitrofluorobenzene ("DNFB"), an aryl halide, as an inhibitor of glycerokinase enzyme was determined.
Materials:
Inhibitor: dinitro-fluorobenzene, Sigma (98%), dilutions were made in absolute ethanol. Following solutions were made:
Solution A: 82.7 mM
Solution B: 8.27 mM
Solution C: 0.827 mM
Protocol: The following samples were prepared using materials described above and previously:

| Sample | Buffer (μl) | ATP (μl) | MgSO4 (μl) | Glycerol (μl) | Glycerokinase (μl) | DNFB (μl, solution) | |
|---|---|---|---|---|---|---|---|
| 1 | 850 | 50 | 10 | 10 | 10 | 100 | A |
| 2 | 850 | 50 | 10 | 10 | 10 | 100 | B |
| 3 | 850 | 50 | 10 | 10 | 10 | 100 | C |
| 4 | 850 | 50 | 10 | 10 | 10 | 100 | ethanol |

Assay: Glycerol was added last to the samples to initiate the enzyme's activity. Before glycerol was added a 50 μl aliquot was taken from all samples as time zero. Next glycerol was added to the samples and after 5, 10 and 15 minutes, 50 μl aliquots were again taken. ATP in all aliquots was measured as described.
Results:

TABLE 3

| Sample | RLU 0 min. | 5 min. | 10 min. | 15 min. | DNFB (mM) |
|---|---|---|---|---|---|
| 1 | 8002 | 7785 | 7965 | 7968 | 8.27 |
| 2 | 7402 | 1585 | 1498 | 1618 | 0.827 |
| 3 | 7025 | 11 | 11 | 18 | 0.0827 |
| 4 | 7230 | 9 | 10 | 11 | 0 |

Conclusions: When the results obtained for samples 1–3 are compared with the results for sample 4(control), it can be seen that while glycerokinase is not effectively inhibited at 0.0827 mM DNFB under the conditions and concentrations used, it is moderately inhibited at 8.27 mM, and effectively inhibited at 0.27 mM DNFB.

EXAMPLE 4

The effect of di-nitrofluorobenzene inhibitor on the bioluminescent assay of ATP was evaluated for use in a method of the invention.
Protocol: The following samples were prepared using materials as described in EXAMPLE 3:

| Sample | Lumit buffer (μl) | ATP (μl) | DNFB (μl, solution) | |
|---|---|---|---|---|
| 1 | 850 | 50 | 100 | A |
| 2 | 850 | 50 | 100 | B |
| 3 | 850 | 50 | 100 | C |
| 4 | 850 | 50 | 100 | ethanol |

Assay: from each sample triplicate 100 μl aliquots were taken. ATP in those aliquots was measured as described.
Results:

TABLE 4

| Sample | RLU 1 | 2 | 3 | mean | % of control | DNFB (mM) |
|---|---|---|---|---|---|---|
| 1 | 14498 | 14780 | 15076 | 14784 | 102.2 | 8.27 |
| 2 | 16060 | 15753 | 15929 | 15914 | 110 | 0.827 |
| 3 | 15157 | 15625 | 15507 | 15429 | 106 | 0.0827 |
| 4 | 13597 | 14203 | 15583 | 14461 | 100 | 0 |

Conclusions: The data in Table 4 shows that DNFB does not interfere with the bioluminescent assay of ATP by firefly luciferase at the DNFB concentrations shown in Example 3 to be effective for inhibition.

EXAMPLE 5

The effectiveness of N-ehtylmaleimide ("NEM") for the inhibition of glycerokinase enzyme was determined.
Materials: Inhibitor: N-ethylmaleimide ("NEM"), Sigma, 416 mM in 16.6% (v/v) ethanol.
Protocol: The following samples were prepared using materials descirbed above and previously:

| Sample | Buffer (μl) | ATP (μl) | MgSO4 (μl) | Glycerol (μl) | Glycerokinase (μl) | NEM (μl) |
|---|---|---|---|---|---|---|
| 1 | 920 | 50 | 10 | 10 | 10 | 50 |
| 2 | 920 | 50 | 10 | 10 | 10 | 40 |
| 3 | 920 | 50 | 10 | 10 | 10 | 30 |
| 4 | 920 | 50 | 10 | 10 | 10 | 20 |
| 5 | 920 | 50 | 10 | 10 | 10 | 10 |
| 6 | 920 | 50 | 10 | 10 | 10 | 0 |

Assay: Glycerol was added last to the samples to initiate the enzyme's activity. Before glycerol was added a 50 μl aliquot was taken from all samples as time zero. At 5, 10 and 15 minutes after addition of glycerol further 50 μl aliquots were taken from the samples. ATP in all aliquots was measured as described.
Results:

TABLE 5

| Sample | 0 min. | 5 min. | 10 min. | 15 min. | NEM (mM) |
|---|---|---|---|---|---|
| 1 | 7406 | 7138 | 6547 | 6820 | 19.8 |
| 2 | 7199 | 7192 | 7002 | 6962 | 16. |
| 3 | 7660 | 7413 | 6812 | 6997 | 12.1 |
| 4 | 7742 | 7130 | 6623 | 6365 | 8.14 |
| 5 | 7635 | 7275 | 6398 | 5922 | 4.10 |
| 6 | 7285 | 13 | 15 | 14 | 0 |

Conclusions: The results for samples 1–5 are compared with the results for sample 6 (no inhibitor, control). At each NEM concentration tested, glycerokinase enzyme seems to be inhibited, the extent of inhibition being somewhat related to the NEM concentration, particularly at 15 minutes.

EXAMPLE 6

The effect of N-ethylmaleimide inhibitor on the bioluminescent assay of ATP was evaluated for use in a method of the invention.

Protocol: The following samples were prepared using materials as described in EXAMPLE 5:

| Sample | Buffer (μl) | ATP (μl) | NEM (μl) |
|---|---|---|---|
| 1 | 950 | 50 | 50 |
| 2 | 950 | 50 | 40 |
| 3 | 950 | 50 | 30 |
| 4 | 950 | 50 | 20 |
| 5 | 950 | 50 | 10 |
| 6 | 950 | 50 | 1 |
| 7 | 950 | 50 | 0 |

Assay: From each sample triplicate 100 μl aliquots were taken and ATP was measured as described.

Results:

TABLE 6

| Sample | 1 | 2 | 3 | mean | % of control | NEM (mM) |
|---|---|---|---|---|---|---|
| 1 | 13534 | 12596 | 12111 | 12747 | 86.3 | 19.8 |
| 2 | 12750 | 13438 | 13448 | 13212 | 89.5 | 16.0 |
| 3 | 14139 | 13794 | 13279 | 13737 | 93.1 | 12.1 |
| 4 | 14401 | 14667 | 14756 | 14608 | 99.0 | 8.14 |
| 5 | 14387 | 14794 | 14051 | 14410 | 97.6 | 4.10 |
| 6 | 15071 | 15081 | 14735 | 14962 | 101.4 | .414 |
| 7 | 14759 | 14643 | 14859 | 14753 | 100.0 | 0 |

Conclusions: NEM interferes only moderately, if at all, with the bioluminescent assay of ATP, at concentrations shown to effectively inhibit the enzyme in EXAMPLE 5.

EXAMPLE 7

The ATP-inactivating activity of the enzyme hexokinase, and its susceptibility to inhibition by p-chloromercuriphenylsulfonic acid inhibitor, were determined at varying concentrations of the enzyme.

Materials:
Inhibitor: p-chloromercuriphenylsulfonic acid ("PCMPSA", Sigma Chemical Co.), 50 mM solution in buffer.
Hexokinase enzyme: Boehringer Mannheim, 140 U/mg, prepared as a stock solution of 10 mg/ml in 3.2 M ammonium sulfate, which was then diluted before use 1:100 with buffer.
Glucose acceptor molecule: Sigma, 100 mg/dl in saturated benzoic acid.

Protocol: Eight samples were prepared using materials described above and previously, as shown in TABLE 7-1 and incubated for various periods of time (i.e., 0, 5, 10 and minutes) before aliquots were taken and assayed as described.

Results:

TABLE 7-1

| Sample | Buffer (μl) | ATP (μl) | Glucose (μl) | Hexokinase (μl) | PCMPSA (μl) | Total Volume (μl) |
|---|---|---|---|---|---|---|
| 1 | 890 | 100 | 10 | — | — | 1000 |
| 2 | 880 | 100 | 10 | 10 | — | 1000 |
| 3 | 870 | 100 | 10 | 20 | — | 1000 |
| 4 | 840 | 100 | 10 | 50 | — | 1000 |
| 5 | 870 | 100 | 10 | — | 20 | 1000 |
| 6 | 860 | 100 | 10 | 10 | 20 | 1000 |
| 7 | 850 | 100 | 10 | 20 | 20 | 1000 |
| 8 | 820 | 100 | 10 | 50 | 20 | 1000 |

TABLE 7-2

| Sample | Hexokinase (U/ml) | PCMPSA (mM) | 0 min (RLU) | 5 min (RLU) | 10 min (RLU) | 15 min (RLU) |
|---|---|---|---|---|---|---|
| 1 | — | — | 29494 | — | 29569 | 29742 |
| 2 | 0.14 | — | — | 12655 | 5549 | 2192 |
| 3 | 0.25 | — | — | 5760 | 464 | 81. |
| 4 | 0.70 | — | — | 460 | 14 | 14 |
| 5 | — | 1.0 | 29494 | — | 29569 | 29742 |
| 6 | 0.14 | 1.0 | — | 25884 | 23717 | 24771 |
| 7 | 0.28 | 1.0 | — | 19116 | 18228 | 16919 |
| 8 | 0.70 | 1.0 | — | 13353 | 11760 | 9375 |

Conclusions: In the presence of increasing concentrations of hexokinase (samples 2–4) and with increasing incubation times, the amount of detectable ATP decreases, presumably as a result of transphosphorylation (i.e., "inactivation") of the ATP by the enzyme. Samples 5–8 show that the inactivating activity of hexokinase can be at least partly inhibited by PCMPSA.

The results also indicate that an effective concentration of PCMPSA alone (i.e., sample 5) in the absence of hexokinase, does not substantially interfere with the subsequent bioluminescent assay.

EXAMPLE 8

Since inhibitor will frequently be added at the same time as a second releasing agent according to the method of the invention, the effect of a commercially available second releasing agent on the inactivating activity of the enzyme hexokinase and on the inhibition of hexokinase by PCMPSA was determined.

Materials: Second releasing agent ("SRA"); mixture of ethoxylated quaternary amine and quaternary ammonium salts (NRB, Lumac/3M).

Protocol: Increasing concentrations of hexokinase, with and without PCMPSA were prepared according to TABLE 8-1 using materials described above and previously.

TABLE 8-1

| Sample | SRA (μl) | ATP (μl) | Glucose (μl) | Hexokinase (μl) | PCMPSA (μl) | Total Volume (μl) |
|---|---|---|---|---|---|---|
| 1 | 890 | 100 | 10 | — | — | 1000 |
| 2 | 880 | 100 | 10 | 10 | — | 1000 |
| 3 | 870 | 100 | 10 | 20 | — | 1000 |
| 4 | 840 | 100 | 10 | 50 | — | 1000 |
| 5 | 870 | 100 | 10 | — | 20 | 1000 |
| 6 | 860 | 100 | 10 | 10 | 20 | 1000 |
| 7 | 850 | 100 | 10 | 20 | 20 | 1000 |

TABLE 8-1-continued

| Sample | SRA (μl) | ATP (μl) | Glucose (μl) | Hexo-kinase (μl) | PCMPSA (μl) | Total Volume (μl) |
|---|---|---|---|---|---|---|
| 8 | 820 | 100 | 10 | 50 | 20 | 1000 |

Results:

TABLE 8-2

| Sample | Hexokinase (U) | PCMPSA (mM) | 0 min (RLU) | 5 min (RLU) | 10 min (RLU) |
|---|---|---|---|---|---|
| 1 | — | — | 26487 | — | 25284 |
| 2 | 0.14 | — | — | 6786 | 1713 |
| 3 | 0.28 | — | — | 2646 | 47 |
| 4 | 0.70 | — | — | 18 | 15 |
| 5 | — | 1.0 | 26457 | — | 25284 |
| 6 | 0.14 | 1.0 | — | 15397 | 15221 |
| 7 | 0.28 | 1.0 | — | 11674 | 12473 |
| 8 | 0.70 | 1.0 | — | 4212 | 3011 |

Conclusions: It can be seen that hexokinase can be sufficiently inhibited with PCMPSA in the presence of SRA. Again, PCMPSA alone seems to show only very slight interference, if at all, with the bioluminescent assay of ATP in SRA.

EXAMPLE 9

The effect of storage at room temperature of a hexokinase:glucose solution was compared in buffer and in a solution containing a first releasing agent. The enzyme of choice will preferably be able to inactivate ATP in the presence of a first releasing agent, since both enzyme and the first releasing agent will typically be present, and possibly even added, simultaneously. Materials:
First releasing agent ("FRA"): ethoxylated alkyl phenol with Na azide preservative (NRS, lumac/3M).
Protocol: Two solutions were prepared using materials described above and previously.
1: hexokinase in buffer: to 1.0 ml of buffer was added 40 μl of the stock hexokinase solution and 20 μl of the stock glucose solution.
2: hexokinase in FRA: to 1.0 ml of FRA was added 40 μl of the stock hexokinase solution and 20 μl of the stock glucose solution.
The two mixtures were stored as such at room temperature. At one hour intervals the activity of hexokinase in the two mixtures was estimated with the following assay:
A. to 50 μl of ATP solution, 50 μl of buffer and 100 μl of Luciferase-luciferin solution was added. ATP was measured as described. Results are listed in column A in TABLE 3-1.
B. to 50 μl of ATP solution, 50 μl of hexokinase in buffer was added. This was allowed to stand for 5 minutes at room temperature. ATP was measured as described. Results are listed in column B of TABLE 3-1.
C. to 50 μl of ATP solution, 50 μl of FRA and 100 ul of Luciferase-luciferin solution was added. ATP was measured as described. Results are listed in column C of TABLE 3-1.
D. to 50 ul of ATP solution, 50 μl of hexokinase in FRA was added and allowed to stand for 5 minutes. ATP was measured as described. Results are listed in column D of TABLE 3-1.
Results:

TABLE 9-1

| | STORAGE CONDITION | | | |
|---|---|---|---|---|
| | Hexokinase in buffer | | Hexokinase in FRA | |
| | A | B | C | D |
| Storage Time (hours) | Starting ATP level (RLU) | Remaining ATP level after 5 minutes (RLU) | Starting ATP level (RLU) | Remaining ATP level after 5 minutes (RLU) |
| 0 | 40808 | 8 | 80814 | 2228 |
| 1 | 38071 | 9 | 50699 | 2662 |
| 2 | 38090 | 11 | 53322 | 1670 |
| 3 | 42020 | 10 | 53809 | 1175 |
| 4 | 38926 | 10 | 54364 | 2519 |
| 5 | 39495 | 13 | 51622 | 1820 |
| 6 | 39479 | 12 | 49937 | 823 |
| 7 | 39801 | 11 | 81499 | 1099 |

Conclusions: It is apparent that, after storage, hexokinase is able to inactivate ATP in solutions containing FRA as well as buffer. Although the residual ATP levels after 5 minutes are consistently higher with hexokinase in FRA than with hexokinase in buffer, they are still consistently low over time, indicating that hexokinase in solution can be stored for at least 7 hours without detriment.

EXAMPLE 10

The ATP-inactivating activity of the enzyme acetate kinase, and its susceptibility to inhibition by PCMPSA, were determined.
Materials:
Acetate kinase enzyme: Boehringer Mannheim, 170 U/mg available as 1 mg/ml in 3.2 M ammonium sulfate.
Magnesium acetate acceptor molecule: Merck, 0.3M in bidistilled water.
Protocol: Samples were prepared as shown in Table 10-1 using materials described above and previously. Acetate kinase was added to initiate enzyme activity. From these samples a 100 μl aliquot was taken at 0, 5, 10 and 15 minutes. ATP in those aliquots was assayed as described.

TABLE 10-1

| Sample | FRA (ml) | Magnesium acetate 3 mM final (μl) | Acetate kinase 1.7 U/ml final (μl) | PCMPSA 0.5 mM final (μl) |
|---|---|---|---|---|
| 1 | 1000 | 10 | — | — |
| 2 | 1000 | — | 10 | — |
| 3 | 1000 | 10 | 10 | — |
| 4 | 1000 | 10 | 10 | 10 |

Each sample also contained: $MgSO_4$ (10 μl) for a final concentration of 5mM, and ATP (100 μl) for a final concentration of 1.0 μg/ml
Results:

TABLE 10-2

| | RLU | | | |
|---|---|---|---|---|
| Sample | 0 min. | 5 min. | 10 min. | 15 min. |
| 1 | 5243 | 5172 | 5185 | 5307 |
| 2 | 5232 | 3316 | 3096 | 2992 |
| 3 | 5221 | 15 | 12 | 15 |
| 4 | 4878 | 2911 | 2263 | 2362 |

Conclusions: The readings for samples 1 and 2 (both serve as control), show that in the absence of acetate kinase enzyme (sample 1) or in the absence of its acceptor molecule, magnesium acetate, (sample 2) the ATP level remains constant throughout the 15 minute test time. The decrease in RLU readings for sample 2 is presumably due to increased quenching caused by the addition of acetate kinase in ammonium-sulfate.

The data for sample 3 show that under the conditions used, acetate kinase with acetate as an acceptor molecule is very effective in inactivating ATP. This is evident from the fact that after 5 minutes the ATP level is reduced to near background levels.

PCMPSA seems to be fairly effective in inhibiting acetate kinase, since there is more ATP detectable in sample 4 (with PCMPSA) as compared to sample 3 (without PCMPSA) at 5, 10 and 15 minutes.

Thus, it is clear that acetate kinase can be used for the inactivation of ATP, and moreover that the enzyme seems to be susceptible to inhibition by PCMPSA.

EXAMPLE 11

The inactivating activity of the enzyme glycerokinase, at a range of concentrations, was compared to that of apyrase over time.

Materials:

Apyrase ("Somase", Lumac/3M lyophilized apyrase, approx. 4.8 U/vial) reconstituted with buffer to 1.0 ml.

Raw milk: local distributor, half-cream, sterilized.

Protocol: Four samples were prepared as shown in TABLE 11-1 using materials described above and earlier, and aliquots taken at 0, 2.5, 5, 10 and 20 minutes.

Results:

TABLE 11-1

| Sample | Raw milk (μl) | FRA (μl) | Glycerol (3.0 mM final) | Glycerokinase (U/ml) | Apyrase (U/ml) |
|---|---|---|---|---|---|
| 1 | 500 | 500 | — | — | 0.096 |
| 2 | 500 | 500 | + | 0.425 | — |
| 3 | 500 | 500 | + | 1.06 | — |
| 4 | 500 | 500 | + | 2.12 | — |

TABLE 11-2

| Sample No. | Glycerokinase (U/mL) | Apyrase (U/mL) | RLU after 0 min. | 2.5 min. | 5 min. | 10 min. | 20 min. |
|---|---|---|---|---|---|---|---|
| 1 | 0 | 0.096 | 64594 | 3272 | 1130 | — | 243 |
| 2 | 0.425 | — | 62641 | 1494 | 613 | 290 | 208 |
| 3 | 1.06 | — | 57863 | 721 | 349 | 230 | 149 |
| 4 | 2.12 | — | 62887 | 245 | 197 | 141 | 107 |

Conclusions: It can be seen that the rate of RLU decrease in the assay changes more during the first 2.5 minutes than during the following 17.5 minutes. In enzyme catalyzed reactions the reaction velocity is frequently dependent, among other things, on the concentrations of the subtrate(s). For glycerokinase, the relevant substrates typically are ATP and glycerol. When glycerol is present in excess, the rate of the reaction is related in large part to the concentration of ATP. As the ATP concentration decreases very rapidly during the test time, the reaction velocity also decreases. The RLU readings observed at 2.5 minutes show that the rate of RLU decrease depends on the amount (U/ml) of glycerokinase used. It can also be seen that if glycerokinase is used at concentrations of 0.425 U/ml or higher, the rate of RLU decrease is significantly faster than with 0.096 U/ml of apyrase (in conventional protocols apyrase is often used at 0.096 U/ml).

EXAMPLE 12

The concentrations of glycerol and magnesium sulfate which provide an optimal activity of glycerokinase were determined.

Using final glycerol concentrations of 1.5, 3, 6, 15 and 30 mM in 50:50 raw milk:FRA solutions, little change was found in the activity of 0.425 U/ml glycerokinase at 5, 10, 20 or 30 minutes of incubation. It seems clear then that a standard glycerol concentration on the order of about 3.0 mM should not be a rate-limiting factor in the inactivation of ATP by 0.425 U/ml glycerokinase.

Similarly magnesium sulfate was assayed at final concentrations of 1, 2, 3, 4, 5 and 10 mM with 0.425 U/ml glycerokinase. Since a slight increase in activity was apparent with increasing concentrations, it is felt that a final concentration of about 5 mM would be satisfactory.

EXAMPLE 13

This experiment simulates the release and measurement of microbial ATP in a solution already containing glycerokinase.

Protocol: Samples were prepared containing: 1000 μl milk (local distributor, half-cream, sterilized); 800 μl FRA, 200 μl of a commercially available first releasing agent which is prepared in buffer for use with samples such as fruit juices (F-NRS, Lumac/3M); and 2.45 mM MgSO$_4$. Glycerol, if present, was at a final concentration of 1.47 mM. Glycerokinase was present at the concentrations indicated in TABLE 13. ATP (10 mg/ml) was added in SRA to begin each assay, and PCMPSA if present, was also in that SRA aliquot in an amount sufficient to yield a final concentration of 0.5 mM.

To begin the assay, 100 μl of SRA/ATP ±PCMPSA was added to 50 μl of the appropriate sample. After 15 seconds (the period normally allowed for microbial nucleotide extraction using SRA) 100 μl Luciferase-luciferin solution was added and ATP was measured as described earlier.

Results:

TABLE 13

| Sample | glycerol (1.47 mM) | glycerokinase (U/ml) | PCMPSA (0.5 mM) | RLU | % Control |
|---|---|---|---|---|---|
| 1 | — | 0.42 | + | 28957 | 100 |
| 2 | — | 1.04 | + | 21901 | 100 |
| 3 | — | 2.06 | + | 15129 | 100 |
| 4 | + | 0.42 | + | 26407 | 91 |
| 5 | + | 1.04 | + | 17213 | 78 |
| 6 | + | 2.06 | + | 6404 | 58 |
| 7 | + | 0.42 | — | 1122 | 4 |
| 8 | + | 1.04 | — | 72 | 1 |
| 9 | + | 2.06 | — | 14 | <1 |

Conclusions: It is clear that glycerokinase is effective (in the absence of PCMPSA) in its inactivating activity in milk-containing samples at each of the concentrations used in samples 7-9. With inhibitor present, the kinetics of the relative reactions become important, as do the relative concentrations and time of addition of reactants. Clearly, given one inhibitor concentration, added with ATP at the same time to each of three concentrations of glycerokinase, the amount of ATP inactivated before the enzyme can be completely inhibited will increase with starting enzyme concentrations. Still, ATP can be detected in each sample and in fact near control levels can be detected when starting enzyme levels are low enough, as in samples 4–6.

EXAMPLE 14

The effectiveness and inhibition of glycerokinase was determined in two different samples frequently tested by bioluminescent assay for microbial contamination - milk and orange juice.

Protocol: Samples with orange juice were prepared with 500 μl orange juice (Riedel, Netherlands, no preservatives, pasteurized), 500 μl buffered FRA, 3 mM glycerol, and with or without 0.5 mM PCMPSA. These were incubated over 0, 5, 10 and 20 minutes at four different glycerokinase concentrations.

Samples with milk were prepared similarly, but using 500 μl raw milk (fresh, local farmer) and 500 μl FRA in place of buffered FRA.

Results:

TABLE 14

| Glycerokinase | | RLU after | | | |
|---|---|---|---|---|---|
| (U/ml) | PCMPSA | 0 min | 5 min | 10 min | 20 min |
| Sample: Orange Juice | | | | | |
| 0.85 | − | 113796 | 3449 | 249 | 146 |
| 0.85 | + | 142369 | 145464 | 150927 | 155082 |
| 1.06 | − | 141794 | 23160 | 1254 | 145 |
| 2.12 | − | 133443 | 5865 | 184 | 140 |
| 2.12 | + | 152487 | 143354 | 132269 | 151899 |
| 4.25 | − | 109249 | 4175 | 162 | 83 |
| 4.25 | + | 116232 | 131999 | 123137 | 125784 |
| Sample: Raw Milk | | | | | |
| 0.85 | − | 952 | 111 | 55 | 38 |
| 0.85 | + | 1382 | 1494 | 1348 | 1280 |
| 1.06 | − | 1093 | 209 | 120 | 54 |
| 2.12 | − | 629 | 140 | 70 | 38 |
| 2.12 | + | 829 | 1340 | 1342 | 1233 |
| 4.25 | − | 502 | 110 | 48 | 34 |
| 4.25 | + | 1173 | 1314 | 1374 | 1028 |

Conclusions: The results of both the orange juice and the milk assays indicate that in the absence of inhibitor even the lowest glycerokinase activity inactivates essentially all of the ATP present in the samples over a period of 20 minutes.

Similarly it can be seen that the chosen inhibitor concentration is sufficient to inhibit even the highest concentrations of enzyme used.

EXAMPLE 16

A commercially-applicable protocol was established for the rapid detection of microorganisms in raw milk samples.

An FRA stock solution was prepared containing 3.0 mM glycerol, and 5.0 mM MgSO$_4$. An SRA stock solution was prepared having 0.5 mM PCMPSA as inhibitor. Immediately before an assay the FRA/glycerol/MgSO$_4$ was used to prepare a solution containing 1.275 U/ml glycerokinase.

Protocol:
1. 25 μl of raw milk is added to a cuvette.
2. 100 μl of the FRA/glycerokinase solution is added
3. The cuvette is left at room temperature for 5 minutes
4. The cuvette is placed in the counting chamber of a photometer.
5. 100 μl of SRA/inhibitor is added.
6. After a 10 or 15 second incubation 100 μl of Luciferase-luciferin solution is added.
7. Light is measured during a 10 second integration interval, and the RLU reading is recorded.

A close correlation is found (coefficient of correlation =0.91) between microbial ATP as detected by the method of this invention, and the number of microbial cells detectable as colony forming units when dilutions of the same samples are plated on plate count agar, incubated at 32° C. for 48 hours and counted by conventional techniques.

I claim:

1. A method for the selective determination of microbial adenosine-triphosphate that is useful for a sample suspected of containing both non-microbial and microbial cells, comprising the steps of:
   (1) selectively releasing non-microbial adenosine triphosphate,
   (2) inactivating substantially all of the released non-microbial adenosinetriphosphate by use of an effective amount of an inactivating enzyme, other than a hydrolase, which can be inhibited by an inhibitor specific for the sulfhydryl groups of enzymes,
   (3) inhibiting substantially all of the inactivating enzyme by use of an effective amount of a specific inhibitor,
   (4) selectively releasing microbial adenosinetriphosphate, and
   (5) detecting a statistically significant amount of the released microbial adenosinetriphosphate by means of an assay.

2. A method according to claim 1 wherein the inactivating enzyme is glycerokinase and the specific inhibitor is p-chloromercuriphenylsulfonic acid.

3. A method according to claim 1 wherein the time required to inactivate the released non-microbial adenosine triphosphate is on the order of ten minutes or less.

4. A method according to claim 1 wherein the inhibitor is selected from the group consisting of N-ethylmaleimide, organomercurials, iodacetate, iodoacetamide, and aryl halides.

5. A method according to claim 1 wherein the inactivating enzyme is a phosphotransferase selected from the group consisting of glycerokinase and adenylate kinase.

6. A method according to claim 1 wherein the assay is a bioluminescent assay.

7. A method according to claim 1 wherein the inhibition of the inactivating enzyme and the release of microbial adenosine triphosphate are carried out simultaneously.

8. A method according to claim 1 wherein the non-microbial adenosine triphosphate is released by a non-ionic releasing agent, and the microbial adenosine triphosphate is released by an ionic releasing agent.

9. A method according to claim 1 wherein the release and inactivation of non-microbial adenosine triphosphate are carried out simultaneoulsy.

* * * * *